United States Patent [19]
Krueger et al.

[11] Patent Number: 5,947,919
[45] Date of Patent: Sep. 7, 1999

[54] INTRALUMINAL SHUNT DEVICE

[75] Inventors: John A. Krueger, Brookfield, Wis.;
Mark M. Levinson, Seattle, Wash.;
Luiz A. Rivetti, Sao Paulo, Brazil

[73] Assignee: Heyer-Schulte NeuroCare, Inc., Pleasant Prairie, Wis.

[21] Appl. No.: 08/864,558

[22] Filed: May 28, 1997

[51] Int. Cl.$^6$ .................................................. A61M 5/00
[52] U.S. Cl. ............................................... 604/8; 604/196
[58] Field of Search ................................ 604/8–10, 194, 604/196

[56] References Cited

U.S. PATENT DOCUMENTS

| | | | |
|---|---|---|---|
| 3,392,722 | 7/1968 | Jorgensen | 604/284 |
| 3,435,824 | 4/1969 | Gamponia | 128/334 |
| 3,515,124 | 6/1970 | Gurchot | 128/1 |
| 3,516,408 | 6/1970 | Montanti | 128/334 |
| 4,142,528 | 3/1979 | Whelan, Jr. et al. | 128/350 R |
| 4,168,708 | 9/1979 | Lepley, Jr. et al. | 128/325 |
| 4,177,813 | 12/1979 | Miller et al. | 128/326 |
| 4,230,119 | 10/1980 | Blum | 128/325 |
| 4,478,219 | 10/1984 | Rozario et al. | 128/325 |
| 4,800,879 | 1/1989 | Golyakhovsky et al. | 128/325 |
| 4,946,463 | 8/1990 | Wright | 606/158 |
| 5,184,610 | 2/1993 | Marten et al. | 128/207.14 |
| 5,330,498 | 7/1994 | Hill | 606/194 |
| 5,360,403 | 11/1994 | Mische | 604/101 |
| 5,374,239 | 12/1994 | Mischenko | 604/8 |
| 5,382,261 | 1/1995 | Palmaz | 606/158 |
| 5,451,235 | 9/1995 | Lock et al. | 606/213 |

OTHER PUBLICATIONS

Rivetti & Gandra, "Myocardial revascularization without cardiopulmonary bypass . . . " Dec. 1991.
Rivetti & Gandra, "Initial Experience Using an Intraluminal Shunt During Revascularization of the Beating Heart"—Dec. 1991.
Bio–Vascular, Inc., "Flo–Rester Disposable Vessel Occluder" Aug. 1, 1994—Product Information Sheet.
Research Medical, Inc., "AnastaFLO Intravascular Shunt"—1995 Product Information Sheet.
Levinson & Fooks, "Coronary Grafting Using a Temporary Intraluminal Shunt . . . ", Dec. 1995, Annals of Thoracic Surgery, pp. 1800–1801.
Mark M. Levinson, "Minimally Invasive Direct Coronary Artery Bypass"—Jun. 16, 1996—MIDCAB Proposal.
Rivetti & Gandra, "Initial Experience Using an Intraluminal Shunt During . . . "—Annals of Thorcic Surgery—Jan. 3, 1997 –63:1742–7.
Luiz A. Rivetti, "Intraluminal Shunting For Off–Pump Coronary Artery Bypass Graft"—May 1997—Hospital Samaritano, Brazil.
Luiz A. Rivetti, "Minimally Invasive Cardiac Surgery" Paper at Minimally Invasive Cardiac Surgery Meeting—Jun. 19–21, 1997 Minneapolis, Minnesota.
Heyer–Schulte NeuroCare, "Myocardial Preservation During Beating Heart Coronary Surgery"—Heart Surgery Forum –www.hsforum.com Appeared on site Nov. 11, 1997.
Heyer–Schulte NeuroCare, Rivetti–Levinson Intraluminal Shunt Product Information Sheet—Mailed Nov. 24, 1997.

*Primary Examiner*—John G. Weiss
*Assistant Examiner*—Ki Yong O
*Attorney, Agent, or Firm*—James A. Geppert

[57] ABSTRACT

A method and apparatus for use in coronary bypass surgery procedures wherein the heart remains beating rather than completely stopping the heart, where a blockage is located in the blood vessel for the heart and an incision is made in the vessel adjacent the blockage for the grafting of a vein from another location in the patient's body, and an intraluminal shunt is inserted into the blood vessel to retain the vessel open and allow blood flow through the vessel but prevent blood flow on the exterior of the shunt. The intraluminal shunt comprises a primary perfusion tube having an enlarged bulb or occluder adjacent each end of the tube to cooperate with the interior surface of the vessel, and a secondary perfusion tube intersecting the primary tube at a point either intermediate between the ends of the primary tube or at a location providing a one-third/two-thirds ratio along the primary tube. In the instance of an intermediate secondary tube, the ends of the primary tube extend beyond the bulbs to terminate in beveled end surfaces. The secondary tube is provided with a cap and the ability to interface the secondary tube with a luer type fitting and may be extended beyond the chest wall of the patient.

14 Claims, 4 Drawing Sheets

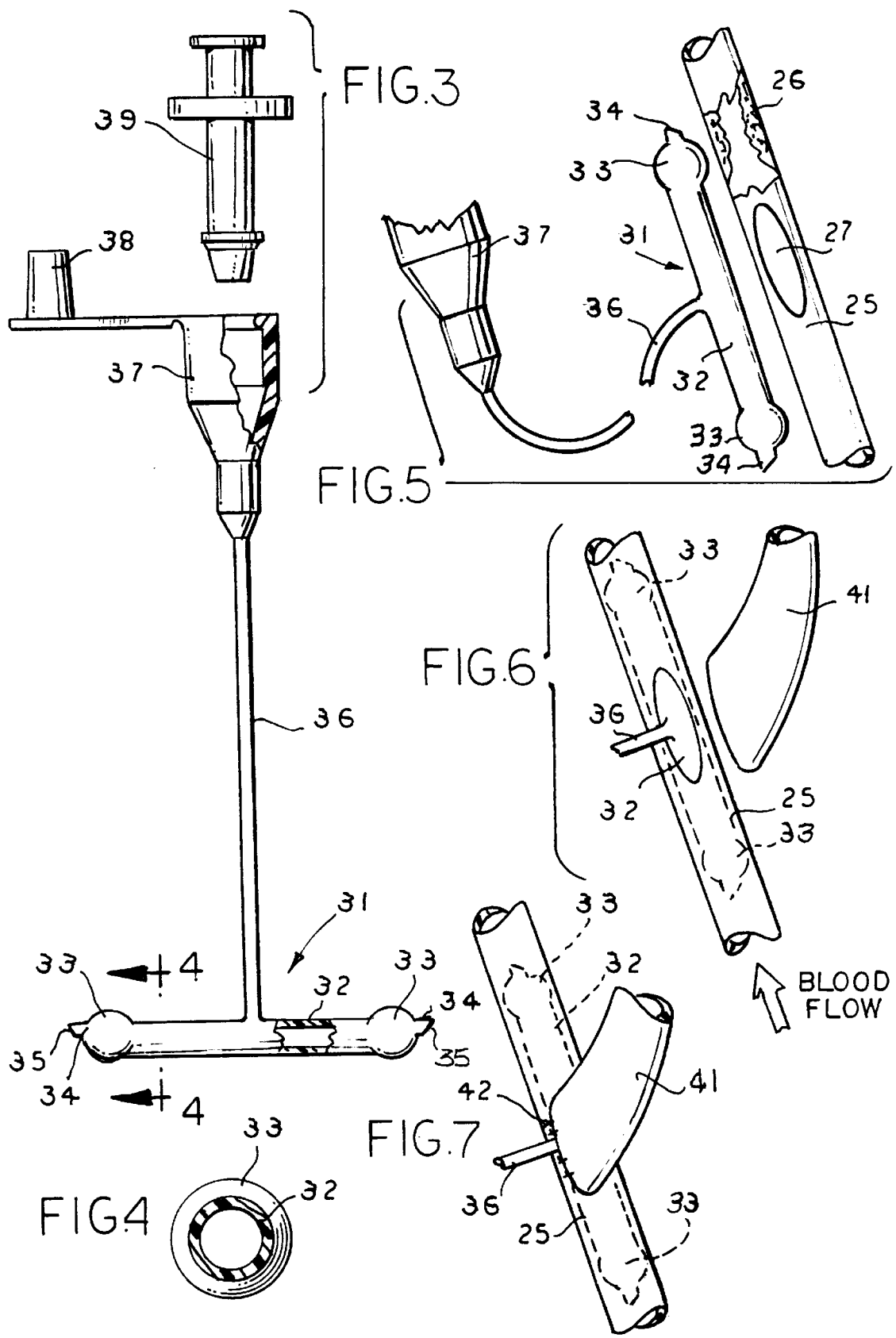

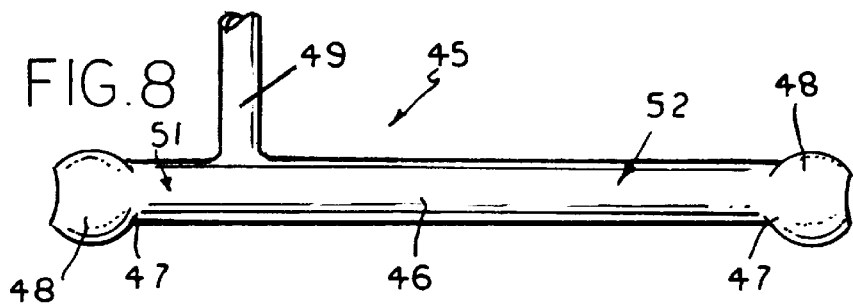
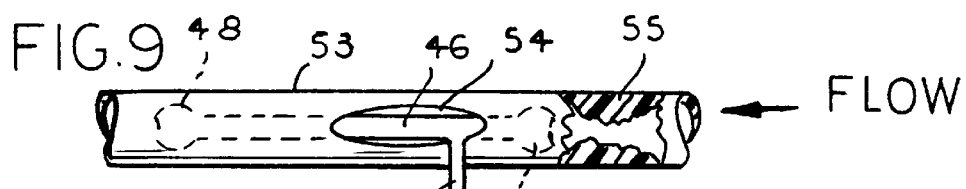
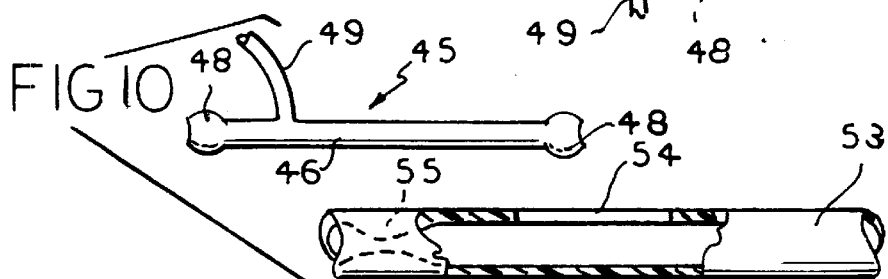
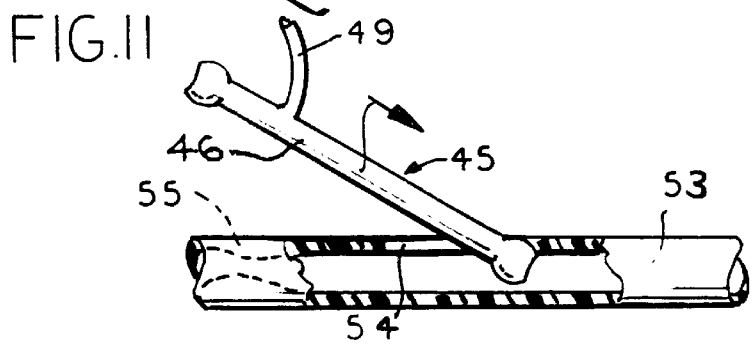
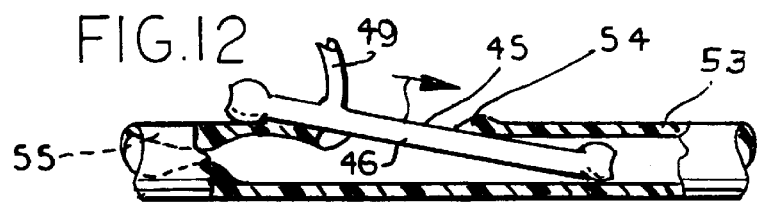
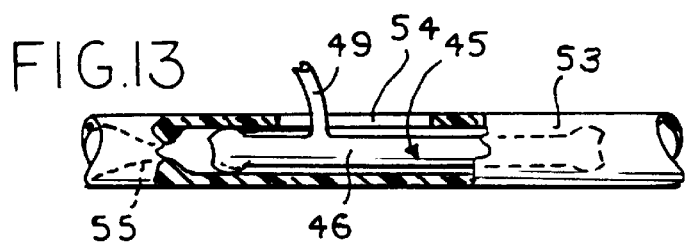

INTRALUMINAL SHUNT DEVICE

TECHNICAL FIELD

The invention disclosed herein relates to an intraluminal shunt device which is utilized in coronary bypass surgery to avoid the usage of a heart/lung machine and the attendant hazards of stopping the heart during the operation.

BACKGROUND

The intraluminal shunt of the present invention relates to a device to be inserted within a blood vessel to allow blood flow during an operation, such as a coronary bypass procedure, wherein the procedure does not involve a heart/lung machine. A relatively common operation in which anastomosis is employed is a coronary artery bypass operation in which blood is routed about a blocked portion of a coronary artery to restore and insure adequate blood supply to the heart muscle. In a conventional heart bypass operation, a short segment of a vein taken from another part of the patient's body is used, with one end of this vein connected to the aorta and the opposite end connected to the blocked coronary artery beyond the blockage. The connection of this vein between the aorta and the coronary artery serves as a bypass around the blockage.

Standard operative technique for providing a coronary artery bypass comprises first clamping off the aorta to occlude blood flow to all the coronary arteries. The bypass connection is then made by suturing the vein in place. Many times multiple bypasses are required and, as a result, it may be necessary for the aorta to be clamped off for an extended period of time during which there is no blood supply to the muscle tissue of the heart or myocardium. The prolonged suspension of blood supply to the heart can result in life threatening infarcts temporarily harming the heart muscle.

To overcome this problem, the vast majority of coronary artery bypass grafting procedures are performed with the assistance of cardiopulmonary bypass (CPB) and cardiac standstill. To stop the heart is traumatic to the patient and may precipitate undesirable ischemic conditions for the patient both during and after completion of the operation. However, an advantage of the use of a heart/lung machine with the attendant stoppage of the beating of the heart for the surgeon is that the heart is motionless and blood-filled, making it technically easier to fashion delicate sutured connections (anastomosis) between the coronary sutures and vein grafts. Thus, the surgery is less stressful and the results are consistent and reproducible from one operation to the next.

In the last decade, there has been progress made in performing bypass grafting without stopping the heart. To accomplish this, a segment of the blocked artery is temporarily occluded and a bypass graft is inserted. However, in these areas, a condition occurs in the patient known as ischemia; i.e., there is a lack of blood in that region from surgical control of the target vessel. This can cause strain on the heart, with changes in the EKG, dangerous rhythm disturbances, or stoppage of the heart beat. Between 15 and 30% of coronary bypass operations done on the beating heart are associated with EKG changes resembling a heart attack. Fortunately, nearly all of these changes are temporary and resolve upon restoration of blood flow in the target vessel. Just the same, there is constant pressure on the surgeon to finish quickly and get the bypass graft open as quickly as possible.

To safely perform coronary bypass grafting without the need to completely arrest the heart, a shunt device has been designed; the shunt providing blood to the starving heart muscle while the surgeon carefully and cautiously constructs the new bypass. The shunt design presented here has many unique features which provide major advantages to the surgeon during off-pump coronary grafting.

SUMMARY OF THE INVENTION

The intracoronary shunt presented in this application is intended to be inserted inside of the target coronary artery and deliver blood to the heart muscle while, at the same time, creating a relatively blood-free zone in the target vessel into which the new bypass graft is connected by fine sutures. Since the heart receives blood flow through the shunt, EKG changes and other deleterious effects common in non-shunt surgical techniques are avoided.

The current design is unique and specialized. Our design features:

1) A flexible tube of silicone, small enough to be inserted completely inside the target coronary artery;
2) Expansion bulbs on each end which fit snugly against the artery and prevent bleeding around the device; and
3) A side port which can be used to remove air, perfuse with blood or specialized medications.

Insertion of this shunt into the target coronary artery during off-pump grafting will:

1) Provide a relatively bloodless operative field;
2) Hold open the edges of the coronary artery, permitting easier suturing;
3) Provide a small space between the bulbs and the main shunt suitable for passing the suture needle without struggling to work around the shunt;
4) Provide blood to the heart muscle during construction of the bypass graft, preventing complications and deleterious effects seen when blood flow is interrupted;
5) Guarantees the sutured connection (anastomosis) is properly constructed when the device slides out without any appreciable resistance; and
6) Reduces the need for the surgeon to hurry, permitting careful and precise construction of these delicate and life-saving bypass grafts.

Our design has additional safety features. The side limb permits the surgeon to connect up to a source of red (oxygen-rich) blood to pump directly into the target coronary artery. This option can be elected if the blood flow through the shunt body is not sufficient. In addition, medications such as blood vessel dilating drugs could be infused into the heart to improve regional function of the heart muscle or alleviate strain.

In addition, our design is adaptable for use during minimally invasive coronary bypass procedures. These new procedures involve construction of bypass grafts to the coronary artery through small surgical incisions for tiny instrument parts inserted into the chest. During these operations, exposure to the heart is very limited, sometimes with the chest cavity entirely closed. Although this strategy is definitely less traumatic to the patient overall, the suturing takes much longer and is considerably more difficult. Our shunt design was created to permit insertion using tiny instruments inserted through the closed chest. Furthermore, a long side part is provided which can exit the chest through a 5 mm. port and be connected to a source of red (oxygen-rich) blood for pumping into the target coronary vessel. This will deliver nutrients to the heart muscle and permit the surgeon to carefully construct the anastomosis even if it takes a long time. For minimally invasive bypass operations, this will be a strong advantage since the technical aspects of suturing through tiny incisions is more difficult and time consuming.

The present invention relates to a new and novel intraluminal shunt which comprises a primary perfusion tube and a secondary perfusion tube integral with and intersecting the primary tube at a generally right angle. An enlarged silicon bulb or occluder is formed adjacent to each end of the primary tube to seal off the leakage of blood around the shunt as well as stent the target vessel open. The bulbs provide isolation of the artery and a blood-free working space, while the primary tube allows blood flow therethrough and retains the artery widely open, which facilitates suturing. The secondary perfusion tube is fashioned to accept a luer connector which then locks onto a source of secondary blood flow from another area of the patient's body, such as the femoral or radial artery, or from an external circulatory assist pump.

Another feature of the intraluminal shunt resides in two differing designs of the shunt depending on a surgeon's suturing technique. A first embodiment locates the secondary perfusion tube at the midpoint of the primary perfusion tube with the bulbs a set distance apart and each end of the primary tube having a beveled tip. The secondary tube provides the ability to infuse drugs through the secondary tube directly into the primary tube and locally into the heart if the occasion requires. The free end of the secondary perfusion tube is fashioned to accept a luer connector or be provided with a Y-type connection with a potential needleless valve.

The present invention also provides a second embodiment of intraluminal shunt wherein the secondary perfusion tube intersects the primary perfusion tube to provide a one-third/two-thirds ratio along the primary tube, thus providing a "heel and toe" arrangement of the primary tube relative to the secondary tube. In this embodiment, the enlarged bulbs are positioned directly at the ends of the primary tube rather than provided with lead-in areas as in the first version. This embodiment lends itself to locations in the target artery where a blockage is very close to the suture line. In either version, the secondary perfusion tube can be elongated to lead to the exterior of the patient's body for use during minimally invasive surgical techniques. The secondary perfusion tube also acts as a handle to aid in removal of the shunt from the target vessel as suturing of the graft is substantially completed.

Another feature of the present invention is that the intraluminal shunt easily adapts itself to more modern techniques where surgery has changed from a large incision to several small incisions as in endoscopic surgery. Thus, a coronary bypass operation can be accomplished through the use of several incisions for an endoscope, an instrument to guide and manipulate the intraluminal shunt and surgical instruments for providing an incision in the artery and for suturing the graft onto the incision during surgery.

BRIEF DESCRIPTION OF THE DRAWINGS

FIG. 3 is a front elevational view of the first embodiment of intraluminal shunt showing possible connection to external instruments.

FIG. 4 is a vertical cross sectional view of the shunt taken on the line 4—4 of FIG. 3.

FIG. 5 is a schematic view of the shunt before insertion into an incision.

FIG. 6 is a schematic view similar to FIG. 5, but with the shunt inserted into the incision in the artery.

FIG. 7 is a schematic view similar to FIG. 6, but showing the graft partially sutured to the artery.

FIG. 8 is a front elevational view of a second embodiment of intraluminal shunt.

FIG. 9 is a top plan view of the shunt of FIG. 8 inserted into the artery adjacent a blockage.

FIG. 10 is an exploded view of the shunt and artery with the artery partially in cross section FIG. 11 is a view similar to FIG. 10, but showing the shunt being inserted into the artery.

FIG. 12 is a front elevational view of the artery partially in cross section with the shunt further inserted therein.

FIG. 13 is a front elevational view similar to FIG. 12, but with the shunt completely inserted in the artery.

BEST MODES OF CARRYING OUT THE INVENTION

Figure 1:
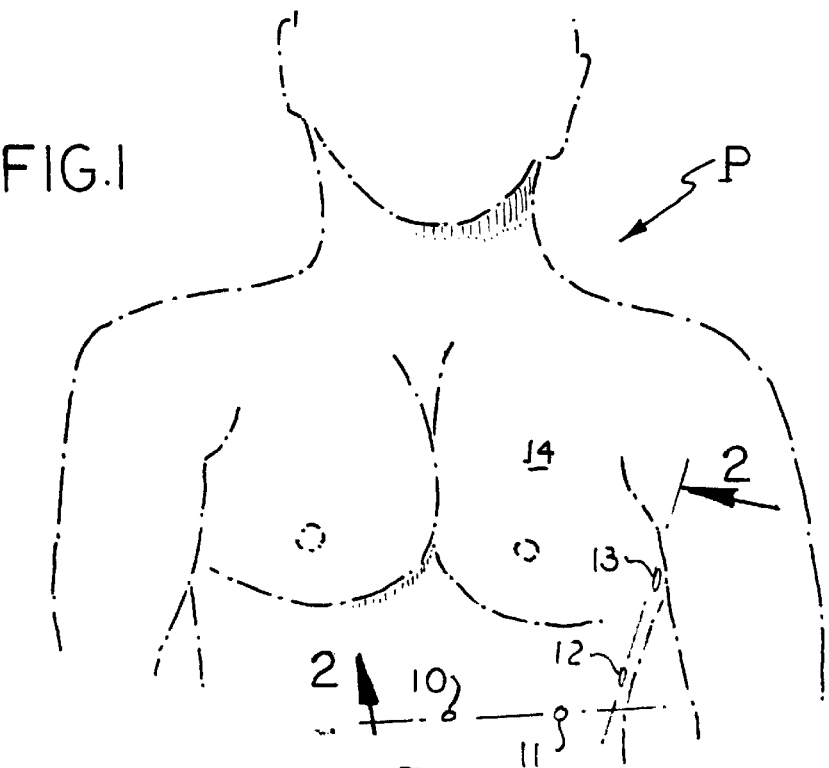
FIG. 1 is a schematic view of a patient for coronary bypass surgery with positions for incisions in the chest wall indicated for thoracoscopic bypass grafting.
Figure 2:
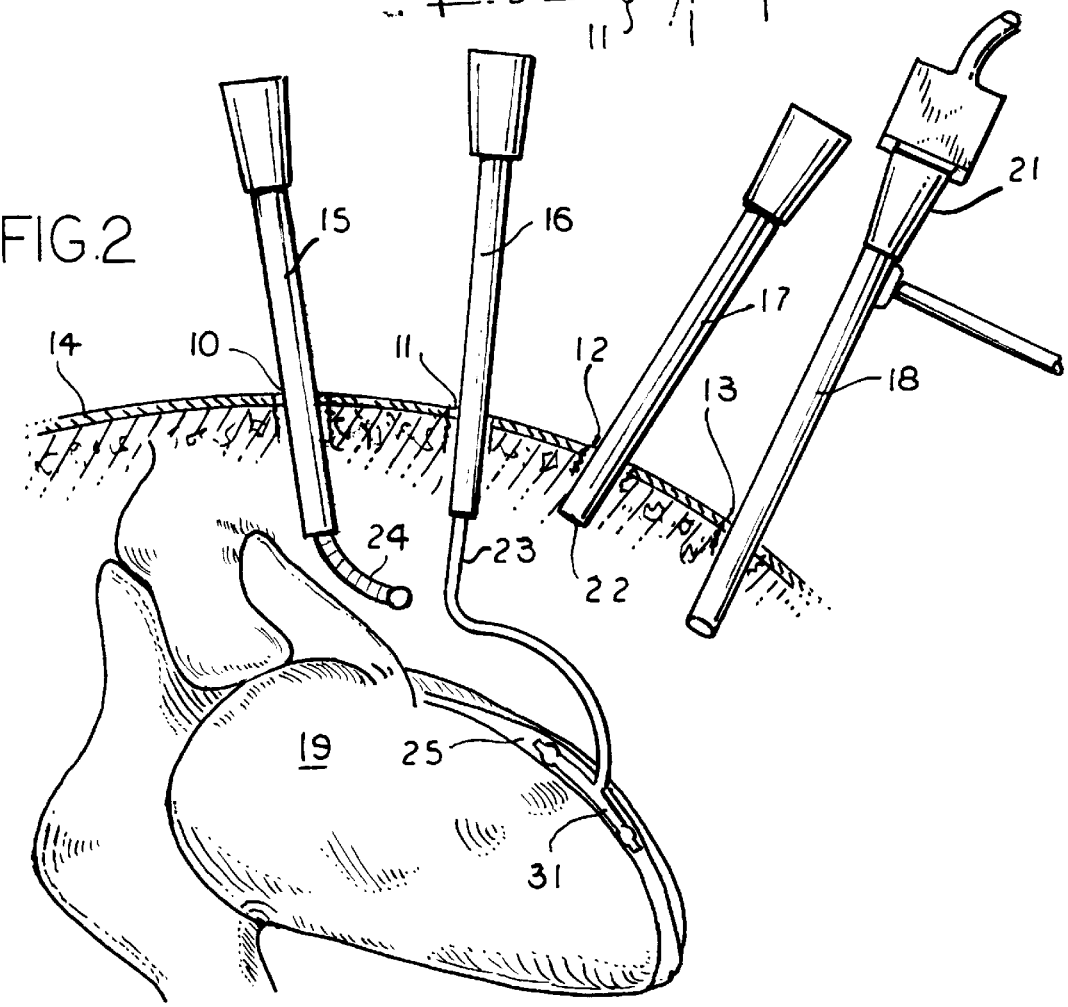
FIG. 2 is a schematic showing of the thoracoscopic instruments extending through small incisions or ports in the chest wall.

Referring more particularly to the disclosure in the drawings wherein are shown illustrative embodiments of the present invention, FIG. 1 discloses a candidate or patient P for coronary bypass surgery with the location of four incisions 10, 11, 12 and 13 in the patient's chest wall 14 shown for use of endoscopic instruments 15, 16, 17 and 18 (see FIG. 2). Unlike previous coronary bypass surgery where the heart is stopped and the patient is kept alive by the circulation of his blood to the brain and vital organs provided by a heart/lung machine, the intraluminal shunt 31 of the present invention allows the heart 19 to remain beating with blood flow through the shunt. As seen in FIG. 2, thoracoscopic instruments 15, 16, 17 and 18 are inserted through the incisions or ports 10, 11, 12 and 13 in the chest wall 14 for access to the patient's heart 19. These instruments include a thoracoscopic camera and fiber optic light 21, endoscope 22, instrument 23 to guide and manipulate the shunt 31, and instruments 24 for operating on the target vessel.

Once a blockage 26 of the target vessel 25 is located, an incision 27 is made adjacent to the blockage 26 which is of sufficient length to allow insertion of the intraluminal shunt 31 into the vessel. As seen in FIG. 3, the intraluminal shunt is formed as a short length of thin wall member or primary perfusion tube 32 having an enlarged occluder or bulb 33 adjacent each end 34, with the opposite ends of the tubing having beveled surfaces or tips 35 at an approximate angle of forty-five degrees. Between the ends of the primary tube 32 is a secondary perfusion tube 36 intersecting the primary tube at an angle of approximately ninety degrees (right angle). In practice, the primary tube is of a length of approximately 2.0 centimeters (cm.) in length with each end 34 extending approximately 3.0 millimeters (mm.) beyond its respective bulb 33, while the secondary tube has a length of approximately 10.0 cm. (or 25 cm.) and is provided with a connector 37 for an interface luer having a closure cap 38 therefor.

To properly size the appropriate shunt for the vessel, various sizes of Garrett probes can be inserted into the blood vessel containing the blockage 26. The appropriate shunt and occluders is selected from the diameter of probe found to be appropriate for the vessel. Also, the secondary tube of a length of approximately 10.0 cm. (or 25 cm.) provides the ability to lock on a secondary blood supply from another area of the body or from an exterior heart pump through a connection 39.

This intraluminal shunt 31 allows blood flow through the target vessel as a graft 41 is sewn onto the incision 27 in the artery and keeps the artery open. Thus, by allowing blood flow and preventing backbleeding due to the bulbs or occluders 33, the shunt increases safety of the coronary bypass operation by allowing sufficient time for suturing the graft 41 onto the incision 27 to reduce the stress on the surgeon performing the operation, provide reproducibility of results from patient to patient and reduce the possibility of ischemic reactions during and after the operation. As the external diameter of the primary tube is smaller than the internal diameter of the blood vessel, suitable spacing is provided between the primary tube and vessel wall to allow the sliding of the sutures into the vessel wall to attach the graft to the incision. As the suturing of the graft 41 at 42 onto blood vessel at the incision nears completion, the intraluminal shunt 31 is gradually withdrawn through the incision by traction on the side limb or secondary tube 36, the final sutures are completed and the suture ends are tied. It has been shown that the use of this shunt reduces suturing time in off-pump coronary bypass procedures by approximately 50%.

Now considering FIGS. 8 through 13, a second embodiment of intraluminal shunt 45 is shown. In this version of shunt, a primary perfusion tube or shunt 46 is provided with enlarged bulbs or occluders 48 at the opposite ends 47 of the shunt and a secondary perfusion tube 49 intersects the primary tube at a point providing a one-third/two thirds ratio resulting in a heel 51 and toe 52 configuration to the uneven ends of the tubing 46 projecting from the intersection of the secondary tube 49 to the primary tube. As seen in FIG. 9, a blood vessel 53 is provided with an incision 54 adjacent a blockage 55 in the vessel. FIGS. 10 through 13 illustrate the gradual insertion of the shunt 45 into the incision 54 in the blood vessel to a position where the occluders completely block the blood flow in the vessel around the shunt but the interior passage formed in the primary tube 46 allows blood flow through the tube so that the heart remains beating during surgery.

As seen in FIGS. 10 through 13, the toe end 52 of the shunt is initially inserted in the vessel incision 54 and gradually worked forward into the interior of the vessel, then the heel 51 is dropped in and engaged by sliding the shunt backward. This is an advantageous technique where the incision must be made close to a blockage and space for insertion of the shunt is limited, with the heel end of the shunt nearest to the blockage. In some cases, it is desirable that the end of the suturing procedure be made in the least critical area and, in the instance of the heel and toe arrangement, the sutures are initially provided adjacent the heel portion for ease of removal of the shunt beginning with the heel portion. Once the graft (not shown) is sutured onto the edges of the incision and as the gradual stitching occurs, the shunt is moved forward, the heel is disengaged and the shunt body is withdrawn. Insertion and withdrawal of the shunt is accomplished by manipulation of the secondary perfusion tube or side limb.

The present invention thus discloses a method and device to provide for substantial non-restrictive blood flow through a blood vessel so that the heart is not stopped during surgery with the attendant possibility of ischemic reactions during or after the construction of a bypass graft. The primary perfusion tube with the attendant occluders at the opposite ends keeps the blood vessel open while allowing blood to flow through the vessel during the operation; the shunt expanding the artery and preventing backbleeding within the blood vessel. If the occasion arises where additional blood is required or one or more drugs are required in the heart, such as a blood thinner, the blood or drug is inserted directly into the heart through the secondary perfusion tube.

Figure 14:
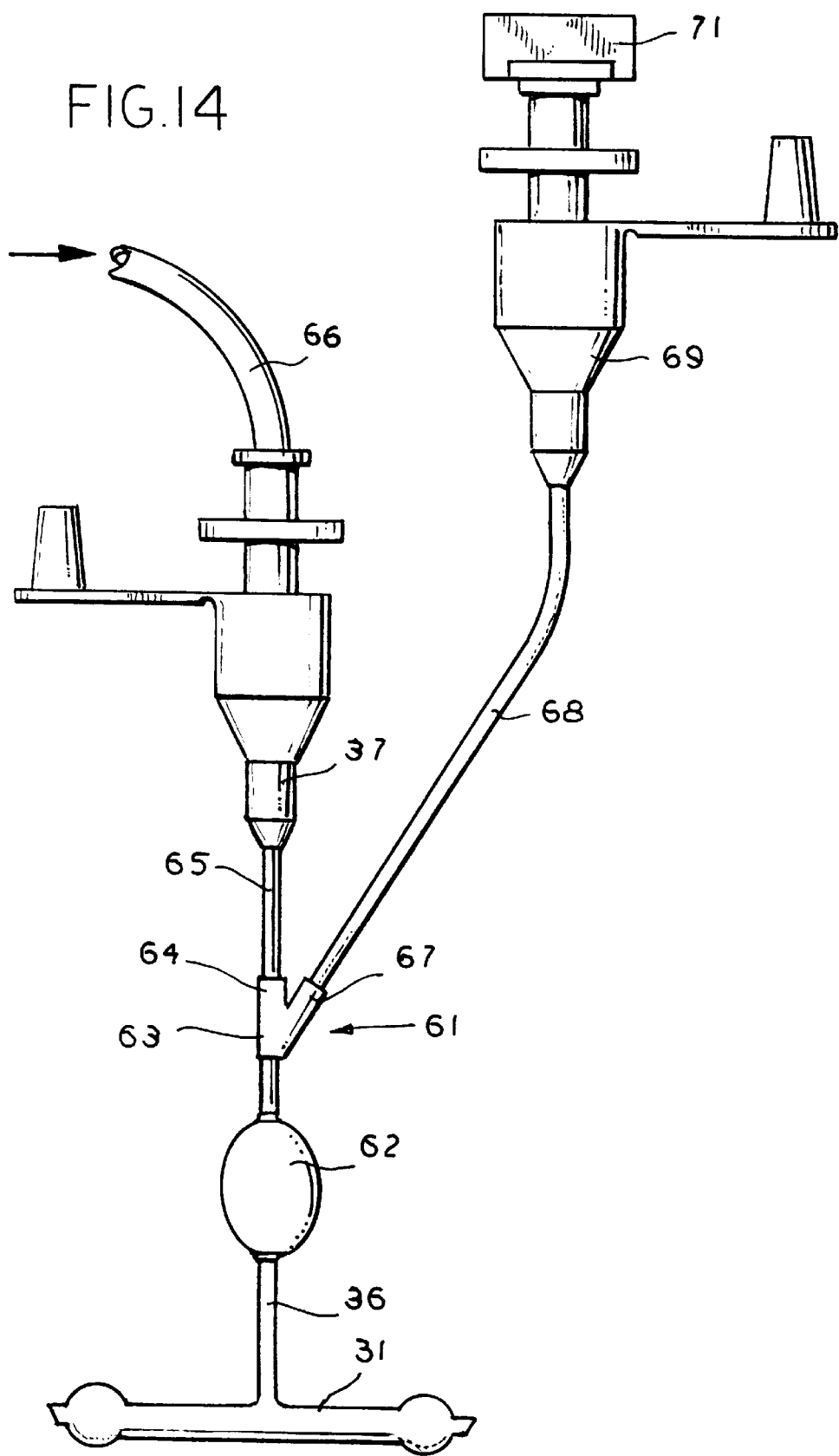
FIG. 14 is a front elevational view of a Y-connector for use in combination with a luer connector.

Considering FIG. 14, a Y-type junction 61 is shown which may be inserted into the secondary perfusion tube 36 and includes an optional mixing chamber 62, a Y-connection 63 having one branch 64 providing an extension 65 of the secondary perfusion tube 36 leading to the luer connector 37 which, in turn, may be connected to a separate blood supply line 66. A second branch 67 of the Y-connection is connected to a drug delivery tubing line 68 that terminates in a second luer connector 69. Attached to this connector may be a needle-less valve 71 so that drugs can be injected into the valve without threat of contamination of the line leading to the shunt. The configuration of the Y-connection will be identical in either embodiment of the primary and secondary perfusion tubes.

Although shown in the drawings for a minimally invasive surgical procedure, either embodiment of the shunt may be utilized for a coronary bypass procedure where surgery includes the opening of the chest wall of the patient and direct operation upon the heart of the patient.

We claim:

1. An intraluminal shunt for coronary procedures acting to retain a blood vessel open and allow blood flow therethrough during procedures such as a coronary bypass, comprising a T-shaped shunt adapted to be inserted and removed through an incision in the blood vessel and including an elongated primary perfusion tube having a first open end, a second open end and a central passage extending between and interconnecting said open ends and a secondary perfusion tube having a first open end and mend open end intersecting with the primary tube and having a central passage extending between said open ends and communicating with said first perfusion tube passage intermediate its ends, an enlarged occluder adjacent each open end of the primary tube to seal the interior of the blood vessel, the primary perfusion tube passage allowing blood flow through the vessel during cardiac or vascular procedures.

2. An intraluminal shunt as set forth in claim 1, wherein said secondary perfusion tube passage intersects the primary perfusion tube passage for fluid communication therewith.

3. An intraluminal shunt as set forth in claim 2, in which said secondary perfusion tube allows connection to an appropriate blood supply.

4. An intraluminal shunt as set forth in claim 2, in which said bulbs are formed of silicon and are slightly greater in diameter than the exterior diameter of said primary perfusion tube.

5. An intraluminal shunt as set forth in claim 4, in which said primary perfusion tube terminates at the enlarged bulbs.

6. An intraluminal shunt as set forth in claim 1, in which the opposite ends of the primary perfusion tube extend beyond the bulbs and terminate in beveled tips or ends.

7. An intraluminal shunt as set forth in claim 1, wherein said secondary perfusion tube intersects said primary perfusion tube in a position providing a one-third/two-thirds division of said primary tube.

8. An intraluminal shunt as set forth in claim 7, wherein said intersection of said primary and secondary perfusion tubes forms a heel and toe arrangement of said primary tube.

9. An intraluminal shunt as set forth in claim 1, in which said secondary perfusion tube is provided with a cap to normally close off said tube.

10. An intraluminal shunt as set forth in claim 1, in which said secondary perfusion tube can be used during an endoscope procedure.

11. An intraluminal shunt as set forth in claim 1, in which a Y-connector is inserted in the secondary perfusion tube to provide a direct line and a second line from the Y-connector for a needle-less valve.

12. An intraluminal shunt as set forth in claim 1, wherein said primary and secondary perfusion tubes are unitary thin wall tubes, with the primary tube being of a slightly smaller exterior diameter than the interior diameter of the blood vessel.

13. An intraluminal shunt as set forth in claim 12, wherein said occluders at the ends of said primary perfusion tube are integral with said tube.

14. An intraluminal shunt as set forth in claim 1, wherein said shunt provides a dual perfusion, completely open system.

* * * * *